United States Patent
Shannon et al.

(10) Patent No.: US 11,523,974 B2
(45) Date of Patent: Dec. 13, 2022

(54) APPARATUS AND METHOD FOR CONTINUOUS MONITORING OF GASTRIC CONTENT VOLUME

(71) Applicants: Samuel Shannon, Even Sapir (IL); Elchanan Fried, Jerusalem (IL)

(72) Inventors: Samuel Shannon, Even Sapir (IL); Elchanan Fried, Jerusalem (IL)

( * ) Notice: Subject to any disclaimer, the term of this patent is extended or adjusted under 35 U.S.C. 154(b) by 831 days.

(21) Appl. No.: 16/461,542

(22) PCT Filed: Nov. 16, 2017

(86) PCT No.: PCT/IL2017/051252
§ 371 (c)(1),
(2) Date: May 16, 2019

(87) PCT Pub. No.: WO2018/092136
PCT Pub. Date: May 24, 2018

(65) Prior Publication Data
US 2019/0350816 A1    Nov. 21, 2019

Related U.S. Application Data

(60) Provisional application No. 62/423,275, filed on Nov. 17, 2016.

(51) Int. Cl.
*A61J 15/00* (2006.01)
*A61B 5/01* (2006.01)
(Continued)

(52) U.S. Cl.
CPC ............. *A61J 15/0084* (2015.05); *A61B 5/01* (2013.01); *A61B 5/4238* (2013.01);
(Continued)

(58) Field of Classification Search
CPC ................ A61J 15/0084; A61J 15/0076; A61J 15/0003; A61M 1/80; A61B 5/01; A61B 5/4238; A61B 5/7264; A61B 5/746
(Continued)

(56) References Cited

U.S. PATENT DOCUMENTS

2012/0323089 A1* 12/2012 Feer .................... A61J 15/0084
600/301
2015/0119953 A1    4/2015 Imran
2016/0206517 A1    7/2016 Elia

FOREIGN PATENT DOCUMENTS

WO    2015120285 A1    8/2015
WO    2016187456 A1    11/2016

OTHER PUBLICATIONS

International Search Report dated Jan. 29, 2018 for PCT application PCT/IL2017/051252.

* cited by examiner

*Primary Examiner* — Phillip A Gray
(74) *Attorney, Agent, or Firm* — Elmore Patent Law Group, P.C.; Joseph C. Zucchero; Carolyn S. Elmore

(57) ABSTRACT

A method and apparatus for determining gastric content volume. The internal temperature of the contents of the stomach is measured at least one predetermined time t after the patient is fed, and the gastric volume determined from the temperature. In preferred embodiments, a known volume of water at a known temperature is injected into the stomach, and the temperature of the stomach contents is measured after the stomach temperature has stabilized. An apparatus for performing the method, in which continuous measurement is possible without disturbing the patient's feeding schedule, and a method for using the inventive method in the control of an automatic feeding apparatus, are also disclosed.

17 Claims, 7 Drawing Sheets

(51) Int. Cl.
*A61B 5/00* (2006.01)
*A61M 1/00* (2006.01)
(52) U.S. Cl.
CPC ............ *A61B 5/7264* (2013.01); *A61B 5/746* (2013.01); *A61J 15/0003* (2013.01); *A61J 15/0015* (2013.01); *A61J 15/0049* (2013.01); *A61J 15/0076* (2015.05); *A61M 1/80* (2021.05); *A61J 2200/72* (2013.01); *A61M 2205/18* (2013.01); *A61M 2205/3303* (2013.01); *A61M 2205/3379* (2013.01); *A61M 2205/50* (2013.01); *A61M 2210/1053* (2013.01); *A61M 2230/50* (2013.01)
(58) Field of Classification Search
USPC ......................................................... 604/503
See application file for complete search history.

US 11,523,974 B2

APPARATUS AND METHOD FOR CONTINUOUS MONITORING OF GASTRIC CONTENT VOLUME

REFERENCE TO RELATED PUBLICATIONS

This application claims priority from U.S. Provisional Pat. Appl. No. 62/423,275, filed 17 Nov. 2016.

FIELD OF THE INVENTION

This invention is directed in general to means and methods for monitoring gastric content volume of patients via a feeding tube such as a nasogastric tube. It is directed in particular to means and methods for continuous monitoring of gastric content volume that are based on thermal measurements and that do not interfere with feeding of the patient.

BACKGROUND OF THE INVENTION

Gastric tubes are commonly used to feed hospital patients, for example, post-operative patients who cannot eat or swallow drugs on their own. While recent research results indicate that small bowel feeding reduces the risk of pneumonia in critically ill patients without affecting mortality, length of stay in the intensive care unit (ICU), or duration of mechanical ventilation, insertion of the post-pyloric tube is cumbersome, and insertion of the nasal jejunal tube usually requires the assistance of a gastroenterologist or radiologist. Thus, due to its ease of administration, gastric tube feeding usually remains the method of first choice for feeding critically ill patients. One problem with gastric tube feeding is that critically ill patients fed via gastric tubes may experience delayed gastric emptying (gastroparesis). Patients receiving enteral feeding are generally monitored closely in order to detect gastroparesis, to assess feeding tolerance, and to prevent aspiration pneumonia.

Efficient monitoring of the patient for intolerance to feedings (e.g. monitoring the patient's status without unnecessary feeding interruptions) remains a major issue in the ICU.

The use of gastric residual volumes (GRVs) for monitoring enteral nutrition (EN) in the ICU setting is highly controversial. Despite the high frequency of use of GRVs in nutrition therapy, there is little experimental data that supports its efficiency. For example, no randomized controlled studies have been reported that suggest that GRV use improves patient outcomes in the ICU. The practice of GRV monitoring was originally designed to help prevent aspiration pneumonia, yet it may actually increase the risk of aspiration pneumonia because it reduces that delivery of EN. The results of measurements of gastric contents depend on factors such as the technique used (e.g. syringe vs. wall suction), tube diameter, position of the patient, etc., and these factors have not been standardized. For example, the interval between GRV measurements may vary, and the "normal" GRV can vary between 50 and 500 $cm^3$. The correlation between GRV and aspiration rate is slim, and no solid data connects the GRV and risk of aspiration to prokinetic therapeutics. GRV measurements also fail to differentiate between normal digestive secretions and the enteral formula, and generally results in unnecessary interruptions of EN. On the other hand, rapid accumulation of a large GRV can result in vomiting and aspiration prior to the next scheduled GRV test.

Other methods of gastric content monitoring include, for example, scintigraphy, paracetamol absorption tests, breath tests, refractometry, ultrasound, and gastric impedance monitoring. Because they tend to be impractical, expensive, and time consuming, and require specialized equipment and frequently skilled operators, these methods are not commonly used in practice.

U.S. Pat. Appl. Pub. No. 2016/0331298 (henceforth '298) discloses methods for estimating gastric content volume. In particular, '298 presents a method for making a qualitative estimation of the gastric content volume based on the rate of change of the temperature of the stomach contents following introduction of a substance at a different temperature than that of the stomach contents. No methods for making a quantitative determination of the gastric content volume are disclosed.

PCT Pat. Appl. Pub. No. WO2016/187456 also discloses a method for estimating gastric content volume in which a substance at a temperature different from that of the stomach contents is introduced into the stomach and the subsequent changes in temperature monitored. The gastric content volume is estimated from the temperature change following introduction of the substance, and a method of calculation of the gastric content volume based on the temperatures, heat capacities, and densities of the substances involved is disclosed. The calculation also includes a purely empirical parameter that is used to compensate for systematic errors. The method typically involves injection of 50 $cm^3$ of water at 1° C. into the stomach. Besides the discomfort of injecting water at such a low temperature, the method suffers from the difficulty that the introduction into the stomach of such a large quantity of water limits the rate at which measurements can be repeated.

Thus, there remains a long-felt but as yet unmet need for means and methods for monitoring gastric content volume that are accurate, precise, and rapid, that can be applied without interfering with patient feeding, that do not require injection of relatively large volumes of material into the stomach, that can be used for continuous monitoring of gastric content volume, and that are inexpensive and do not require specialized equipment or training.

SUMMARY OF THE INVENTION

The present invention is designed to meet this as yet unmet need. The invention comprises a novel method and apparatus for monitoring gastric content volume that is based on thermodilution methods.

It is therefore an object of this invention to disclose a method for determining gastric content volume $V_t$ in a patient, comprising: measuring a temperature $T_f$ of content of said patient's stomach at least one predetermined time t after a predetermined time $t_0$; and, determining said gastric content volume from the temperature so determined.

It is a further object of this invention to disclose such a method, wherein said method comprises determining a temperature $T_0$ of said content of said patient's stomach at or before said time $t_0$, and said step of determining said gastric content volume comprises calculating said gastric content volume based on a comparison of $T_0$ and $T_f$.

It is a further object of this invention to disclose a method as defined in any of the above, comprising introducing a predetermined volume $V_{in}$ of enteral nutriment characterized by a temperature $T_{in}$, wherein said time $t_0$ is a time not later than a time of introduction of said enteral nutriment. In preferred embodiments of the invention in which the method comprises a step of introducing enteral nutriment, $V_{in}$<50 cm³. In more preferred embodiments, $V_{in}$<20 cm³. In particularly preferred embodiments of the invention in which the method comprises a step of introducing enteral nutriment, $V_{in}$ is between 1 and 5 cm³. In some preferred embodiments of the invention in which the method comprises a step of introducing enteral nutriment, said step of introducing enteral nutriment comprises introducing a predetermined volume of water.

In some preferred embodiments of the invention in which the method comprises a step of introducing enteral nutriment, said content of said patient's stomach is characterized by a temperature $T_0$ at a predetermined time not later than $t_0$, and $|T_0-T_{in}| \leq 30°$ C.

In some preferred embodiments of the invention in which the method comprises a step of introducing enteral nutriment, said step of introducing a predetermined volume of enteral nutriment is performed such that said enteral nutriment mixes with said content of said patient's stomach with a mixing time below a predetermined maximum $t_{max}$. In some preferred embodiments, $t_{max} \leq 60$ s. In some particularly preferred embodiments, $t_{max} \leq 30$ s.

In some preferred embodiments of the invention in which the method comprises a step of introducing enteral nutriment, said enteral nutriment is characterized by a density $\rho_{in}$, and said step of determining said gastric content volume does not comprise any step selected from the group consisting of: (a) measuring $\rho_{in}$; (b) performing a calculation in which a value of $\rho_{in}$ is explicitly included; and, (c) performing a calculation comprising an equation in which a term explicitly depending on $\rho_{in}$ is included.

In some embodiments of the invention in which the method comprises a step of introducing enteral nutriment, said step of introducing enteral nutriment comprises introducing said enteral nutriment into a balloon located within said stomach, and said method comprises removing said enteral nutriment from said balloon after said step of measuring temperature $T_f$.

It is a further object of this invention to disclose the method as defined in any of the above, wherein: said method comprises introducing a predetermined volume $V_{in}$ of enteral nutriment characterized by a temperature $T_{in}$ and a heat capacity $C_p^{in}$; said content of said stomach is characterized by a heat capacity $C_p^0$ and a temperature $T_0$ prior to said step of introducing enteral nutriment; and, said step of determining said gastric content volume comprises calculating said gastric content volume according to a relation $$V_t = \frac{C_p^{in}}{C_p^0} \frac{T_{in} - T_f}{T_f - T_0} V_{in},$$

where $T_f$ is a temperature of the stomach contents at time t. In some preferred embodiments of the method, $V_{in}$<50 cm³. In more preferred embodiments, $V_{in}$<20 cm³. In some particularly preferred embodiments of the method, $V_{in}$ is between 1 and 5 cm³. In some preferred embodiments of the invention, said step of introducing enteral nutriment comprises introducing a predetermined volume of water. In some preferred embodiments of the invention, said content of said patient's stomach is characterized by a temperature $T_0$ at a predetermined time not later than $t_0$, and $|T_0-T_{in}| \leq 30°$ C. In some embodiments, said step of introducing a predetermined volume of enteral nutriment is performed such that said enteral nutriment mixes with said content of said patient's stomach with a mixing time below a predetermined maximum $t_{max}$. In some preferred embodiments, $t_{max} \leq 60$ s. In some particularly preferred embodiments, $t_{max} \leq 30$ s.

It is a further object of this invention to disclose a method as defined in any of the above, wherein said method comprises: introducing into said stomach a device configured to alter said temperature of said content of said patient's stomach; and, activating said device at time $t_0$.

It is a further object of this invention to disclose a method as defined in any of the above, wherein a machine learning protocol is used to produce a model of a relationship between said internal temperature at time t and said gastric content volume.

It is a further object of this invention to disclose a method as defined in any of the above, wherein a machine learning protocol is used to refine a pre-existing model of a relationship between said internal temperature at time t and said gastric content volume.

It is a further object of this invention to disclose a method as defined in any of the above, wherein a revaluation method is used to produce a model of a relationship between said internal temperature at time t and said gastric content volume.

It is a further object of this invention to disclose a method as defined in any of the above, wherein a revaluation method is used to refine a pre-existing model of a relationship between said internal temperature at time t and said gastric content volume.

It is a further object of this invention to disclose a method as defined in any of the above, wherein said step of measuring an internal temperature comprises independently measuring an internal temperature at a plurality of times. In some preferred embodiments of the invention, each pair of said plurality of times is separated by a predetermined interval $\Delta t$. In some preferred embodiments of the invention, said step of determining said gastric content volume comprises: determining a temperature $T_0$ of said contents of said stomach at a time not later than $t_0$; and, determining said gastric content volume from a rate at which said temperature of said contents of said stomach returns to $T_0$.

It is a further object of this invention to disclose a method as defined in any of the above, wherein said method comprises providing a warning if said calculated gastric content volume is outside of predetermined limits.

It is a further object of this invention to disclose a method as defined in any of the above, wherein said method comprises providing a warning if said calculated gastric content volume indicates that said patient needs to be fed.

It is a further object of this invention to disclose a method as defined in any of the above, wherein said method comprises pumping out of said stomach at least a portion of said gastric content if at least one condition selected from the group consisting of (a) said calculated gastric content volume is observed to have increased at a rate above a predetermined maximum; and (b) said gastric content volume is above a predetermined maximum is met.

It is a further object of this invention to disclose a method as defined in any of the above, wherein said method comprises producing an output signal proportional to said calculated gastric content volume. In some preferred embodiments, said step of producing an output signal comprises providing a signal configured to direct a control system of an automatic feeding apparatus to perform an action selected from the group consisting of increasing a rate of feeding, decreasing a rate of feeding, increasing a volume of feeding, decreasing a volume of feeding, stopping feeding, and starting feeding. In some preferred embodiments, said step of determining said gastric content volume from said internal temperature comprises calculating said gastric content volume from said internal temperature at a plurality of times $t_n$; and, said step of producing an output signal comprises producing a plurality of output signals, each one independently based on said calculated gastric content volume at each time $t_n$. In some particularly preferred embodiments, each pair of said plurality of times are separated by a predetermined interval $\Delta t$. In some preferred embodiments, the method comprises (a) transmitting said output signal to a controlling means for controlling a feeding pump; (b) converting said output signal to a control signal configured to control said feeding pump connected to said controlling means; and (c) using said control signal to set a value of at least one parameter selected from the group consisting of rate of introduction of enteral nutriment by said feeding pump into said stomach and volume of enteral nutriment introduced into said stomach by said feeding pump, said value of said parameter determined from said calculated gastric content volume.

It is a further object of this invention to disclose a method as defined in any of the above, wherein said method is performed by using an apparatus comprising:
  a flexible tube comprising a proximal end and a distal end and characterized by an outer diameter sufficiently small to fit into a nasogastric tube leaving sufficient space for enteral nutriments to pass through;
  a temperature measuring device configured to produce a temperature-dependent signal in connection with said flexible tube; and,
  a control/readout device configured to convert said temperature-dependent signal into a temperature reading, said control/readout device in connection with said flexible tube.

In some preferred embodiments of the invention in which the method is performed on the aforementioned apparatus, at least one of said temperature measuring device and said flexible tube is disposable. In some particularly preferred embodiments of the invention, said temperature measuring device is selected from the group consisting of thermistors and thermocouples.

In some preferred embodiments of the invention in which the method is performed on the aforementioned apparatus, the method comprises determining whether said nasogastric tube has been inserted into said patient's stomach or into said patient's lung. In some particularly preferred embodiments, said step of determining whether said nasogastric tube has been inserted into said patient's stomach or into said patient's lung comprises: (a) measuring a time-dependent temperature profile following said time $t_0$; and, (b) determining whether said time-dependent temperature profile is consistent with a profile expected following insertion of said nasogastric tube into a lung or with a profile expected following insertion of said nasogastric tube into a stomach.

In some preferred embodiments of the invention in which the method is performed on the aforementioned apparatus, said method comprises introducing through said flexible tube a predetermined volume of enteral nutriment characterized by a temperature $T_{in}$, wherein said time $t_0$ is a time not later than a time of introduction of said enteral nutriment. In some preferred embodiments of the method, $V_{in} \leq 50$ cm$^3$. In more preferred embodiments, $V_{in} \leq 20$ cm$^3$. In some particularly preferred embodiments of the method, $V_{in}$ is between 1 and 5 cm$^3$. In some preferred embodiments of the invention, said step of introducing enteral nutriment comprises introducing a predetermined volume of water. In some preferred embodiments of the invention, said content of said patient's stomach is characterized by a temperature $T_0$ at a predetermined time not later than $t_0$, and $|T_0 - T_{in}| \leq 30°$ C. In some embodiments, said step of introducing a predetermined volume of enteral nutriment is performed such that said enteral nutriment mixes with said content of said patient's stomach with a mixing time below a predetermined maximum $t_{max}$. In some preferred embodiments, $t_{max} \leq 60$ s. In some particularly preferred embodiments, $t_{max} \leq 30$ s.

It is a further object of this invention to disclose an apparatus for determining gastric content volume, comprising:
  a flexible tube comprising a proximal end and a distal end and characterized by an outer diameter sufficiently small to fit into a nasogastric tube while leaving sufficient space for enteral nutriments to pass through and an inner diameter sufficiently;
  at least one temperature measuring device attached to said flexible tube, said temperature measuring device configured to produce a temperature-dependent signal; and,
  control/readout means in connection with said flexible tube, said control/readout means configured: (a) to convert said temperature-dependent signal into a temperature reading, said control/readout means; and (b) to determine, from a time-dependent temperature profile obtained from said temperature measuring device, whether said flexible tube has been inserted into a lung or into a stomach of a patient.

It is a further object of this invention to disclose such an apparatus, wherein said temperature measuring device comprises at least one device selected from the group consisting of thermistors and thermocouples.

It is a further object of this invention to disclose an apparatus as defined in any of the above, wherein at least one of said temperature measuring device and said flexible tube is disposable.

It is a further object of this invention to disclose an apparatus as defined in any of the above, wherein at least one of said flexible tube and said temperature measuring device is thermally insulated.

It is a further object of this invention to disclose an apparatus as defined in any of the above, wherein said flexible tube is incorporated integrally into a nasogastric feeding tube. In some embodiments, said flexible tube is disposed within a wall of said nasogastric feeding tube. In some embodiments, said flexible tube is disposed spirally about a longitudinal axis of said nasogastric feeding tube.

It is a further object of this invention to disclose an apparatus as defined in any of the above, wherein said apparatus comprises a device configured to alter a temperature of content within a stomach, said device disposed at said distal end of said flexible tube.

It is a further object of this invention to disclose an apparatus as defined in any of the above, wherein said flexible tube is characterized by an internal diameter that is different at said proximal end than it is at said distal end.

It is a further object of this invention to disclose an apparatus as defined in any of the above, wherein said distal end of said flexible tube comprises a plurality of openings.

It is a further object of this invention to disclose an apparatus as defined in any of the above, wherein said distal end of said flexible tube is attached to a balloon, said balloon configured to be inflated by material exiting said distal end of said flexible tube.

It is a further object of this invention to disclose an apparatus as defined in any of the above, wherein said apparatus comprises enteral nutriment introduction means configured to inject a predetermined volume $V_{in}$ of enteral nutriment into a stomach via said flexible tube.

In some preferred embodiments of the invention in which the apparatus comprises said apparatus comprises enteral nutriment introduction means, said apparatus comprises computing means configured to compute a gastric content volume according to a relation $$V_t = \frac{C_p^{in}}{C_p^0} \frac{T_{in} - T_f}{T_f - T_0} V_{in},$$

where $C_p^{in}$ and $C_p^0$ are heat capacities of said injected enteral nutriment and contents of said stomach, respectively, and $T_{in}$, $T_f$, and $T_0$ are temperatures of said injected enteral nutriment, said stomach contents at time t, and said stomach contents prior to injection of said enteral nutriment, respectively.

In some preferred embodiments of the invention in which the apparatus comprises said apparatus comprises enteral nutriment introduction means, said enteral nutriment introduction means are configured to introduce enteral nutriment into a stomach of a patient at a plurality of predetermined times. In some particularly preferred embodiments, each pair of said plurality of predetermined times are separated by a predetermined interval.

In some preferred embodiments of the invention in which the apparatus comprises said apparatus comprises enteral nutriment introduction means, said enteral nutriment introduction means are configured to mix enteral nutriment introduced through said flexible tube with said content of said patient's stomach with a mixing time below a predetermined maximum $t_{max}$. In some preferred embodiments, $t_{max} \leq 60$ s. In some particularly preferred embodiments, $t_{max} \leq 30$ s.

It is a further object of this invention to disclose an apparatus as defined in any of the above, comprising computing means configured to use a machine learning protocol to produce a model of a relationship between said internal temperature at time t and said gastric content volume.

It is a further object of this invention to disclose an apparatus as defined in any of the above, comprising computing means configured to use a machine learning protocol to refine a pre-existing model of a relationship between said internal temperature at time t and said gastric content volume.

It is a further object of this invention to disclose an apparatus as defined in any of the above, comprising computing means configured to use a revaluation method to produce a model of a relationship between said internal temperature at time t and said gastric content volume.

It is a further object of this invention to disclose an apparatus as defined in any of the above, comprising computing means configured to use a revaluation method to refine a pre-existing model of a relationship between said internal temperature at time t and said gastric content volume.

It is a further object of this invention to disclose an apparatus as defined in any of the above, comprising communication means configured to communicate a signal proportional to a calculated gastric content volume to an external device.

In some preferred embodiments of the apparatus in which it comprises communication means configured to communicate a signal proportional to a calculated gastric content volume to an external device, said external device comprises a pump configured to pump out at least a portion of said gastric content if said signal rises at a rate above a predetermined maximum.

In some preferred embodiments of the apparatus in which it comprises communication means configured to communicate a signal proportional to a calculated gastric content volume to an external device, said external device comprises control means for controlling an automatic feeding apparatus.

In some preferred embodiments of the apparatus in which it comprises communication means configured to communicate a signal proportional to a calculated gastric content volume to an external device, said communication means is selected from the group consisting of hardwired data transfer, wireless data transfer, and electrical connection.

It is a further object of this invention to disclose the method as defined in any of the above, performed on the apparatus as defined in any of the above.

It is a further object of this invention to disclose the use of the apparatus as defined in any of the above in a method for determining gastric content volume in a patient, wherein said method comprises: (a) measuring an internal temperature of said patient's stomach at least one predetermined time t after a predetermined time $t_0$; and (b) determining said gastric content volume from said internal temperature.

It is a further object of this invention to disclose such a use, wherein said method comprises measuring a temperature $T_0$ of said content of said patient's stomach at or before said time $t_0$, and said step of determining said gastric content volume comprises calculating said gastric content volume based on a comparison of $T_0$ and $T_f$.

It is a further object of this invention to disclose the use as defined in any of the above, wherein said method comprises introducing a predetermined volume $V_{in}$ of enteral nutriment characterized by a temperature $T_{in}$, wherein said time $t_0$ is a time not later than a time of introduction of said enteral nutriment. In some preferred embodiments, $V_{in} \leq 50$ cm$^3$. In more preferred embodiments, $V_{in} \leq 20$ cm$^3$. In some especially preferred embodiments, $V_{in}$ is between 1 and 5 cm$^3$. In some preferred embodiments, said content of said patient's stomach is characterized by a temperature $T_0$ at a predetermined time not later than $t_0$, and $|T_0 - T_{in}| \leq 30°$ C. In some particularly preferred embodiments, said step of introducing enteral nutriment comprises introducing a predetermined volume of water. In some embodiments, said enteral nutriment is characterized by a density $\rho_{in}$, and said step of determining said gastric content volume does not comprise any step selected from the group consisting of: measuring $\rho_{in}$; performing a calculation in which a value of $\rho_{in}$ is explicitly included; and, performing a calculation comprising an equation in which a term explicitly depending on $\rho_{in}$ is included.

In some embodiments of the use in which the method includes a step of introducing a predetermined volume of enteral nutriment, said step of introducing a predetermined volume of enteral nutriment is performed such that said enteral nutriment mixes with said content of said patient's stomach with a mixing time below a predetermined maximum $t_{max}$. In some preferred embodiments, $t_{max} \leq 60$ s.

In some embodiments of the invention in which the method includes a step of introducing enteral nutriment, said step of introducing enteral nutriment comprises introducing said enteral nutriment into a balloon located within said stomach, and said method comprises removing said enteral nutriment from said balloon after said step of measuring temperature $T_f$.

It is a further object of this invention to disclose the use as defined in any of the above, wherein:
  said method comprises introducing a predetermined volume $V_1$ of enteral nutriment characterized by a temperature $T_{in}$ and a heat capacity $C_p^{in}$;
  said content of said stomach is characterized by a heat capacity $C_p^0$ and a temperature $T_0$ prior to said step of introducing enteral nutriment; and,
  said step of determining said gastric content volume comprises calculating said gastric content volume according to a relation $$V_t = \frac{C_p^{in}}{C_p^0} \frac{T_{in} T_f}{T_f T_0} V_{in}$$

where $T_f$ is a temperature of the stomach contents at time t.

It is a further object of this invention to disclose the use as defined in any of the above, wherein said method comprises: introducing into said stomach a device configured to alter said temperature of said content of said patient's stomach; and activating said device at time $t_0$.

It is a further object of this invention to disclose the use as defined in any of the above, wherein said step of measuring an internal temperature comprises independently measuring an internal temperature at a plurality of times. In some preferred embodiments of the invention, each pair of said plurality of times is separated by a predetermined interval $\Delta t$.

It is a further object of this invention to disclose the use as defined in any of the above, wherein said method comprises providing a warning if said calculated gastric content volume is outside of predetermined limits.

It is a further object of this invention to disclose the use as defined in any of the above, wherein said method comprises providing a warning if said calculated gastric content volume indicates that said patient needs to be fed.

It is a further object of this invention to disclose the use as defined in any of the above, wherein said method comprises pumping out of said stomach at least a portion of said gastric content if at least one condition selected from the group consisting of: (a) said calculated gastric content volume is observed to have increased at a rate above a predetermined maximum; and (b) said gastric content volume is above a predetermined maximum; is met.

It is a further object of this invention to disclose the use as defined in any of the above, wherein said method comprises producing an output signal proportional to said calculated gastric content volume. In some embodiments of the invention, said step of producing an output signal comprises providing a signal configured to direct a control system of an automatic feeding apparatus to perform an action selected from the group consisting of increasing a rate of feeding, decreasing a rate of feeding, increasing a volume of feeding, decreasing a volume of feeding, stopping feeding, and starting feeding. In some embodiments of the invention, said step of determining said gastric content volume from said internal temperature comprises calculating said gastric content volume from said internal temperature at a plurality of times $t_0$; and said step of producing an output signal comprises producing a plurality of output signals, each one independently based on said calculated gastric content volume at each time $t_0$. In some preferred embodiments of the invention, each pair of said plurality of times is separated by a predetermined interval $\Delta t$. In some embodiments of the invention, said method comprises: transmitting said output signal to a controlling means for controlling a feeding pump; converting said output signal to a control signal configured to control said feeding pump connected to said controlling means; and, using said control signal to set a value of at least one parameter selected from the group consisting of rate of introduction of enteral nutriment by said feeding pump into said stomach and volume of enteral nutriment introduced into said stomach by said feeding pump, said value of said parameter determined from said calculated gastric content volume.

It is a further object of this invention to disclose a method for determining whether a nasogastric feeding tube has been inserted into a stomach or into a lung, comprising: measuring a time-dependent temperature profile following a time $t_0$; and, determining whether said time-dependent temperature profile is consistent with a profile expected following insertion of said nasogastric tube into a lung or with a profile expected following insertion of said nasogastric tube into a stomach. In some preferred embodiments of the method, such a method, wherein said time $t_0$ is prior to feeding said patient.

It is a further object of this invention to disclose a method for controlling an automatic feeding apparatus comprising a control system and configured to introduce enteral nutriment into a stomach, said method comprising: determining a gastric content volume of said stomach according to the method defined in any of the above; producing an output signal proportional to said gastric content volume; transmitting said output signal to said control system; and, using said control system to control a value of at least one parameter selected from rate of introduction of enteral nutriment into said stomach and volume of enteral nutriment introduced into said stomach, said value determined by a predetermined protocol from said output signal.

It is a further object of this invention to disclose a method for controlling an automatic feeding apparatus as defined above, wherein said automatic feeding apparatus is a feeding pump.

It is a further object of this invention to disclose a method for controlling an automatic feeding apparatus as defined in any of the above, wherein said control system is configured to direct said automatic feeding apparatus according to at least one protocol selected from the group consisting of: adjusting said value of said at least one parameter so as to maintain said gastric content volume within predetermined limits; increasing said value of said at least one parameter if said gastric content volume is below a predetermined minimum; decreasing said value of said at least one parameter if said gastric content volume is above a predetermined maximum; stopping said automatic feeding apparatus if said gastric content volume is above a predetermined maximum; and, starting said automatic feeding apparatus if said gastric content volume is below a predetermined minimum. In some preferred embodiments, said predetermined maximum is that volume that yields a gastric content volume consistent with a condition selected from the group consisting of imminent aspiration of content of said stomach; imminent regurgitation of content of said stomach; occurrence of aspiration of content of said stomach; and, occurrence of regurgitation of content of said stomach.

It is a further object of this invention to disclose the use of the apparatus as defined in any of the above in a method for controlling an automatic feeding apparatus comprising a control system and configured to introduce enteral nutriment into a stomach, wherein said method comprises: using said apparatus to determine a gastric content volume of said stomach as defined in any of the above; producing an output signal proportional to said gastric content volume; transmitting said output signal to said control system; and, using said control system to control a value of at least one parameter selected from rate of introduction of enteral nutriment into said stomach and volume of enteral nutriment introduced into said stomach, said value determined by a predetermined protocol from said output signal. In some preferred embodiments of the invention, said automatic feeding apparatus is a feeding pump.

It is a further object of this invention to disclose the use defined above of the apparatus as defined in any of the above in a method for controlling an automatic feeding apparatus, wherein said control system is configured to direct said automatic feeding apparatus according to at least one protocol selected from the group consisting of: adjusting said value of said at least one parameter so as to maintain said gastric content volume within predetermined limits; increasing said value of said at least one parameter if said gastric content volume is below a predetermined minimum; decreasing said value of said at least one parameter if said gastric content volume is above a predetermined maximum; stopping said automatic feeding apparatus if said gastric content volume is above a predetermined maximum; and, starting said automatic feeding apparatus if said gastric content volume is below a predetermined minimum. In some preferred embodiments, said predetermined maximum is that volume that yields a gastric content volume consistent with a condition selected from the group consisting of imminent aspiration of content of said stomach; imminent regurgitation of content of said stomach; occurrence of aspiration of content of said stomach; and, occurrence of regurgitation of content of said stomach.

It is a further object of this invention to disclose the use of the apparatus as defined in any of the above in a method for determining a health status of a patient, wherein said method comprises: obtaining a time profile of gastric content volume of said patient by determining a gastric volume by the method as defined in any of the above at a plurality of times following introduction of a known volume of enteral nutriment into said a stomach of said patient; and, comparing said time profile with a time profile characteristic of a healthy individual who has ingested an equal volume of enteral nutriment.

It is a further object of this invention to disclose the use defined above of the apparatus as defined in any of the above in a method for determining a health status of a patient, wherein said method comprises using results of said step of comparing in order to make a prognosis of a likelihood that future feedings will lead to an abnormal time profile of gastric content volume.

It is a further object of this invention to disclose the use of the apparatus as defined in any of the above in a method for determining a health status of a patient as defined in any of the above, wherein said method comprises using results of said step of comparing in order to design a treatment protocol for said patient.

BRIEF DESCRIPTION OF THE DRAWINGS

The invention will now be described with reference to the drawings, wherein.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. In particular, any combination of individual elements or method steps that are disclosed herein that is not self-contradictory is considered to be within the scope of the invention, even if that particular combination is not explicitly recited.

As used herein, the term "feeding tube" refers to any tube that passes solids or liquids directly to the stomach or to the intestines. Non-limiting examples of feeding tubes include nasogastric tubes and percutaneous endoscopic gastrostomy (PEG) tubes.

As used herein, the term "enteral nutriment" refers to any substance that can be introduced into the stomach via a nasogastric feeding tube.

Figure 3A:
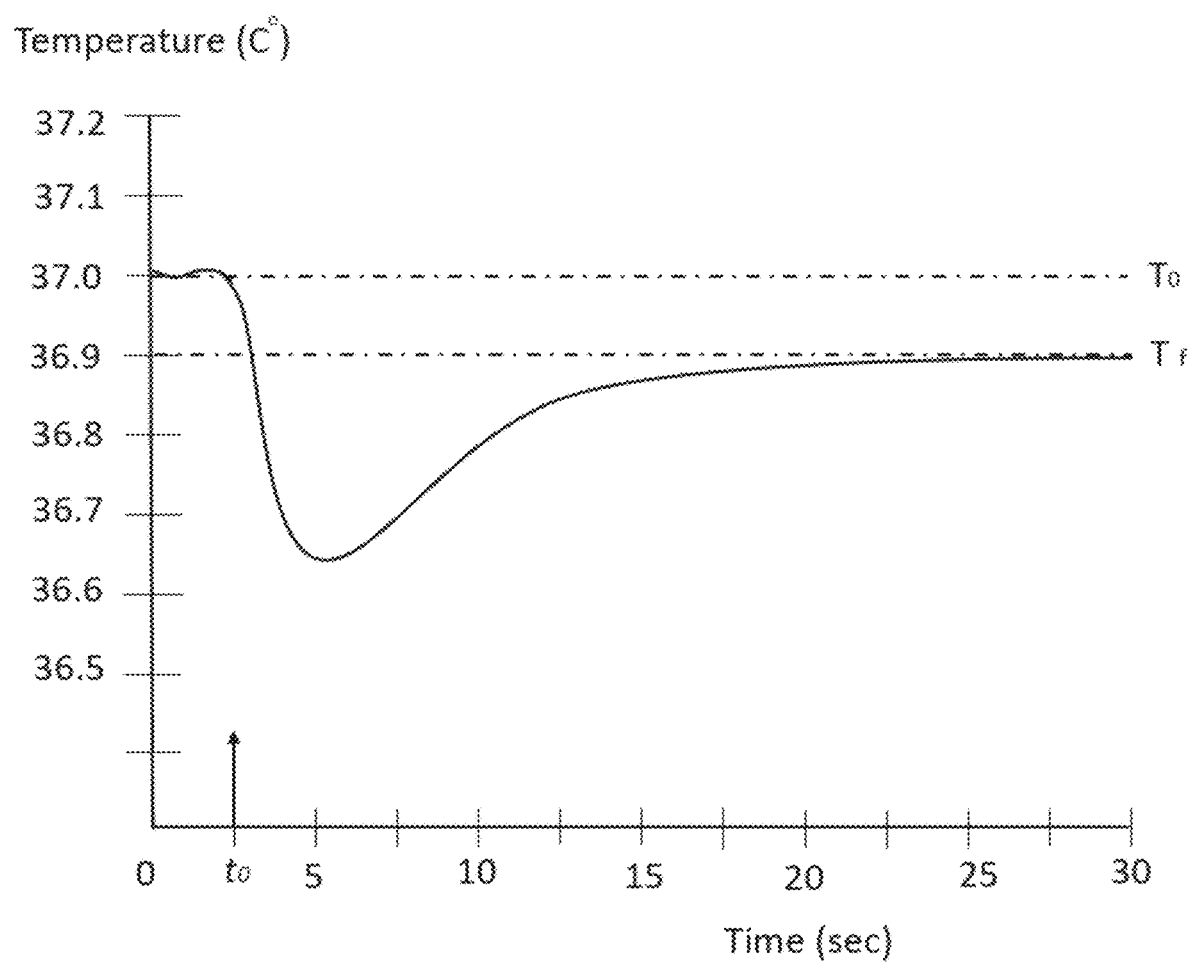
FIGS. 3A and 3B present graphs illustrating typical profiles of the temperature in the stomach following injection of enteral nutriment according to one embodiment of the invention herein disclosed, on two different time scales (30 s and 70 s, respectively)
Figure 3B:
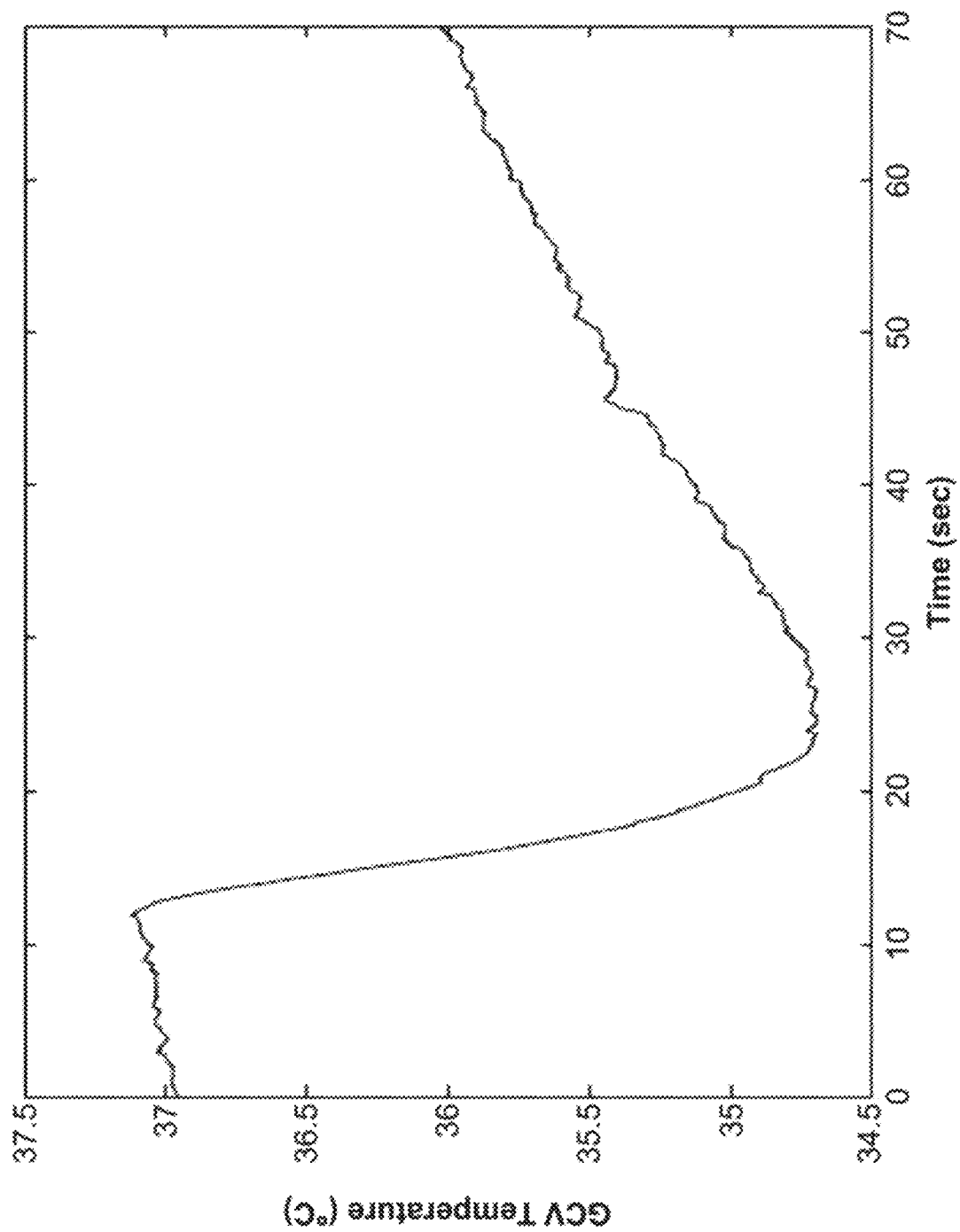

In contrast to means and methods known in the art, the present invention uses a thermodilution method for estimating the gastric content volume. The basic principle of the inventive method is that when enteral nutriment is injected into the patient's stomach, the temperature inside the stomach undergoes a rapid (near-instantaneous) decrease followed by a relatively rapid rise to a nearly constant pseudo-equilibrium temperature that will depend on the gastric content volume, followed by a much slower return to body temperature as the nutriment passes through the stomach. In preferred embodiments of the invention, the injection of enteral nutriment used to determine the gastric content volume is separate from the regular feeding of the patient. Non-limiting example of a typical temperature profile following injection of enteral nutriment at time $t_0$ are illustrated in FIGS. 3A and 3B.

Since the difference between the pseudo-equilibrium temperature following introduction of enteral nutriment and the temperature preceding the injection will depend on the gastric content volume (i.e. the volume of the contents within the stomach), it is thus possible to determine the gastric content volume at any arbitrary time t after the temperature within of the stomach contents has stabilized, since the time-dependent temperature can be modeled mathematically.

In contrast to methods known in the art, the components used in the inventive method and system disclosed herein are small enough to pass through the feeding tube while leaving room for injection of additional enteral nutriment. The inventive method can be used to make continuous measurements without interrupting the patient's feeding schedule, and indeed can be made even when the feeding is continuous, and, as explained in detail below, can be done with the use of far smaller amounts of injected material than are used in methods known in the prior art. Moreover, the method can be used with any kind of feeding tube (non-limiting examples of which include nasogastric tubes and percutaneous endoscopic gastrostomy (PEG) tubes); the components are inexpensive, thereby enabling use of disposable (single-use) components; and the method does not require specialized equipment or training for its implementation.

The inventive method comprises measuring the internal temperature of the stomach at a time t after a predetermined time $t_0$. In preferred embodiments of the invention, $t_0$ is the time that enteral nutriment is injected into the stomach, and t is a time following $t_0$ sufficiently such that the temperature of the gastric content has reached $T_f$. The gastric content volume is then calculated from the known time/temperature relationship discussed above. In preferred embodiments of the invention, the temperature measurements are made continuously, thereby giving a continuous profile of the gastric content volume. In preferred embodiments of the invention, the gastric content volume $V_t$ at time t following injection of enteral nutriment is estimated according to eq 1:

$$V_t = \frac{C_p^{in}}{C_p^0} \frac{T_{in} - T_f}{T_f - T_0} V_{in} \quad (1)$$

where $V_{in}$ is the volume of the injected enteral nutriment, $C_p^{in}$ and $C_p^0$ are the heat capacities of the injected enteral nutriment and the stomach contents, respectively, and $T_{in}$, $T_f$, and $T_0$ are the temperatures of the injected enteral nutriment, the stomach contents at time t, and the stomach contents prior to injection of the enteral nutriment ($t_0$), respectively. $T_f$ will typically be the pseudo-equilibrium temperature at which the stomach contents stabilizes following the injection of the enteral nutriment. We note that in contrast to literature methods of determining gastric content volume by thermodilution methods, the inventive method (e.g. as exemplified in the embodiment given in eq (1)) does not involve any explicit calculation of, or have any explicit reliance on, the density of the injected enteral nutriment or of the stomach contents.

While in principle, the method can be used following injection of any type of enteral nutriment, in preferred embodiments of the invention, the enteral nutriment used to estimate the gastric content volume is a known volume of water at a known temperature $T_{in}$, which is typically (but not necessarily) less than body temperature. Since the heat capacity of water is well-known and the volume of the injected water can easily be controlled, calculating $V_t$ by using eq (1) is straightforward when the injected enteral nutriment is water. In typical embodiments of the invention, an aliquot of water having a volume of less than 20 cm³, preferably 1-5 cm³, and a temperature of 10-25° C. (i.e. less than 30° C. below body temperature, and typically about 20° C. below body temperature) is injected. The injection is typically done by use of a syringe, but any device known in the art for injecting fluid into a small-diameter tube can be used.

Because the amounts of material that are used are typically so small, the method can be performed with only a relatively small interval between successive injections of enteral nutriment. In some preferred embodiments of the invention, the determination of the gastric content volume is done repeatedly at intervals of 10-15 minutes, although smaller or larger intervals are considered by the inventors to be within the scope of the invention.

In some embodiments of the inventive method such as those in which the determination of the gastric content volume is done according to eq (1), the temperature at time t is the pseudo-equilibrium temperature to which the stomach contents stabilize after injection of the enteral nutriment, as shown in FIG. 3A. The return to the pseudo-equilibrium temperature will occur on a time scale related to the mixing time between the injected enteral nutriment and the stomach contents. Because the components of the inventive system, described in detail below, are smaller than those known in the art, and because the enteral nutriment is typically injected under pressure (e.g. from the syringe or other injector), the mixing time in the inventive system in method is much faster than that of methods known in the art. The mixing time typically occurs on a time scale in which the mixing is complete within a time ($t_{max}$) is ≤60 s. As shown in FIG. 3A, in preferred embodiments of the invention, $t_{max}$ of 30 s or less is readily achieved.

In some embodiments of the invention, the gastric content volume is calculated from the rate at which the temperature of the stomach content returns to body temperature, which occurs on a longer time scale than the approach to the pseudo-equilibrium temperature, as illustrated in FIG. 3B.

In some embodiments of the method, rather than injection of enteral nutriment, the temperature of the stomach content is changed by use of a heating or cooling element of a type known in the art that has been introduced into the stomach. The heating or cooling element is activated at time $t_0$, and the rate and/or magnitude of the temperature change following activation of the heating or cooling element is used to determine the gastric content volume.

In some embodiments of the invention, rather than injection of the enteral nutriment directly into the stomach, a balloon is attached to the tube through which the enteral nutriment is injected. Injection of the enteral nutriment inflates the balloon. After the temperature measurements are complete, the enteral nutriment is removed from the balloon via the tube through which it was introduced (e.g. by use of a syringe).

In some embodiments of the invention, the basic model relating the estimated gastric content volume to the measured temperature at time t is supplemented, refined, or replaced by equations developed from machine learning algorithms. Such algorithms are well-known in the art, and any appropriate machine learning method may be applied. Similarly, in some embodiments of the invention, the basic model relating the estimated gastric content volume to the measured temperature at time t is supplemented, refined, or replaced by equations developed from revaluation methods known in the art.

In some preferred embodiments of the invention, an alarm or warning to the operator is given if the circumstances warrant it. Non-limiting examples of conditions under which an alarm or warning would be given include the gastric content volume is low enough that the patient needs to be fed; the temperature at time t is outside of predetermined limits; the gastric content volume is determined to have risen at a rate above a predetermined maximum; and, $T_f$ varies by more than a predetermined amount or the time/temperature profile deviates from the mathematical relation given above by more than a predetermined amount, thereby indicating a problem such as regurgitation and/or aspiration of the stomach content. For example, a sudden increase in the gastric content volume may indicate that the patient is about to vomit. In the inventive system, an increase in gastric content volume would manifest itself as an increase in $T_0-T_f$, in extreme cases as near-constant temperature following injection of enteral nutriment rather than a return of the temperature to equilibrium according to eq 1. In such a case, an alarm would be provided to the system operator or to a caregiver that the temperature profile is outside of its expected limits indicating that the patient may be about to vomit.

The warning may be of any type known in the art; non-limiting examples include visual warnings (e.g. flashing lights), auditory warnings (e.g. a beep), a warning message produced on the panel of a control apparatus, and a warning sent to a cell phone (e.g. that of the patient's physician or of the operator of the system). In preferred embodiments of the inventive method, it is performed using the inventive apparatus disclosed herein and described in detail below. In some embodiments of the invention, alternative measurements of the stomach contents such as refractometry are made in parallel with the thermodilution method.

In some embodiments of the invention, the method comprises pumping out at least part of the gastric content (e.g. with a stomach pump of any appropriate design known in the art) if the gastric content volume rises at a rate above a predetermined maximum. As explained above, a rapid rise in gastric content volume may indicate that the patient is about to vomit, and in order to prevent this event from occurring, the method includes pumping the stomach until the gastric content volume is restored to an acceptable level.

In some embodiments of the invention, the inventive method for calculating the gastric content volume is used as the basis for a method for controlling the introduction of enteral nutriment into a patient's stomach. The calculated gastric volume is used to generate a signal that is then used to determine the rate of introduction of food. While the signal can be presented visually or aurally to a caregiver who then adjusts the rate of feeding manually, in preferred embodiments, the signal is passed on to the control system for an automatic feeding apparatus such as a feeding pump. The input signal received by the control system for the automatic feeding apparatus is then converted into an output signal that is then used to control the volume or rate of enteral nutriment introduced into the stomach. As non-limiting examples, if the gastric volume is determined to have exceeded a predetermined maximum, the introduction of enteral nutriment by the feeding apparatus can be stopped, while if it is below a predetermined minimum and no enteral nutriment is being introduced into the stomach, the introduction can be started or restarted. The input signal can also be calibrated such the rate or volume of introduction of enteral nutriment can be raised or lowered in order to keep the gastric volume within predetermined bounds. The control system may comprise any means known in the art for controlling the automatic feeding apparatus, as can the means by which the calculated volume is converted to the signal transmitted to the control system and this signal converted internally into a command to the automatic feeding system to start, stop, or alter the feeding rate or amount.

In some embodiments of the invention, it is used as part of a method to determine the health status of a patient. In a healthy patient, after introduction of a bolus of food of known volume, the gastric content volume will rise and then fall as the food passes through the stomach. In some embodiments of the invention disclosed herein, the gastric content volume is measured at intervals (typically every few minutes) following introduction of a bolus of food, and the resulting profile compared with that of a healthy individual. If the profile deviates from that of a healthy individual (e.g. the stomach empties much more slowly than is expected), then the caregiver will be aware that the patient is not digesting his or her food properly. In some embodiments of the invention, the comparison is done by a computer programmed to make such comparisons, and the caregiver alerted if a deviation from a healthy profile is observed. The method can be repeated with introduction of boluses of differing volumes to determine whether the patient has a digestive problem that manifests itself only when a volume above or below a given threshold is ingested.

Similarly, the method disclosed herein can be used to monitor nearly continuously the gastric content volume of a patient, and if there are repeated deviations from the expected volume, the caregiver will know (or can be alerted, as explained above) that there is a problem.

The method disclosed herein can thus be used in order to help a caregiver make a prognosis of the patient's condition. Non-limiting examples include an assessment of the likelihood that the patient will regurgitate food after a feeding, that the stomach will take more or less time than usual to empty, and what kind of care will be necessary to treat the observed time-dependent behavior of the gastric content volume.

In preferred embodiments of the invention, it includes a method and apparatus for determination of whether the feeding tube has been inserted into the stomach or into the lungs. A time-dependent temperature profile is obtained; in preferred embodiments, the temperature profile is obtained prior to introduction of enteral nutriment into the feeding tube, i.e. prior to the start of feeding of the patient. If the feeding tube has been properly inserted into the stomach, then the temperature should be constant or near constant. On the other hand, if the feeding tube has been inserted into a lung, then it is expected that the temperature profile following its insertion will comprise periodic dips in the measured temperature with each breath as air that is cooler than body temperature enters the lungs, followed by a return to body temperature. By comparing the observed temperature profile with those expected from the two cases, the location of the feeding tube (i.e. proper insertion into the stomach or accidental insertion into a lung) can be determined.

Figure 1A:
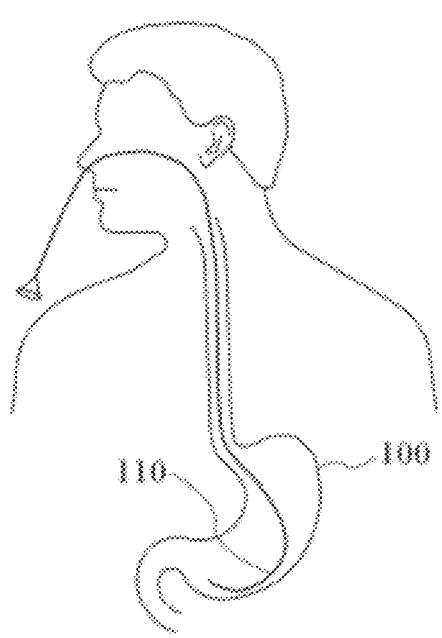
FIGS. 1A-1C present schematic illustrations of one embodiment of the apparatus of the present invention in situ.
Figure 1B:
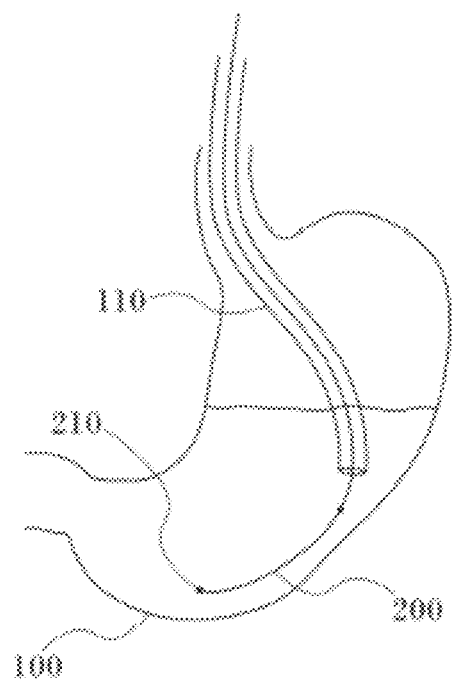
Figure 1C:
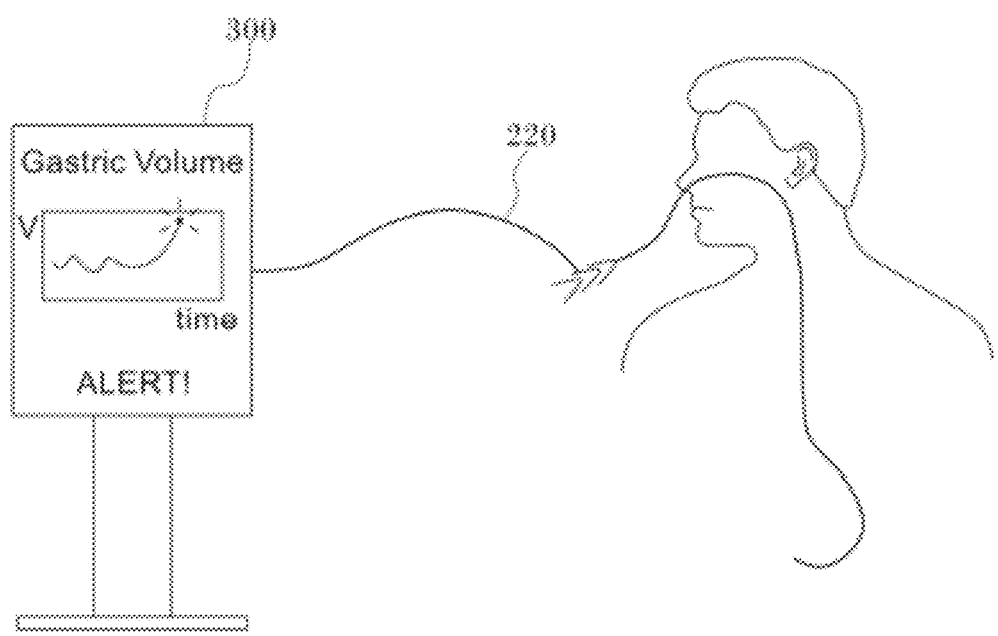

It is within the scope of the invention to disclose an apparatus designed to perform the inventive method. Reference is now made to FIG. 1, which shows schematically an in situ arrangement of one non-limiting embodiment of the apparatus disclosed in the present invention. FIG. 1A shows a patient with a nasogastric tube 110 in place with its distal end inside the patient's stomach 100. FIG. 1B shows a closer schematic view of the patient's stomach 100 with the distal end of nasogastric tube 110 and the distal end of one embodiment of the apparatus herein disclosed. The apparatus comprises a flexible tube 200 connected at its distal end to at least one temperature measuring device 210 configured to measure the temperature inside the stomach. In preferred embodiments, the temperature measuring device is a thermocouple or thermistor. In some embodiments, a plurality of temperature measuring devices (typically 8-12) are located along the flexible tube. In preferred embodiments, the flexible tube includes an electrically insulated wire that that can pass a signal from the temperature measuring device to a controller or monitor. In preferred embodiments, the flexible tube passes through the nasogastric tube into the stomach, with its distal end extending beyond the distal end of the nasogastric tube. The diameter of the flexible tube is sufficiently small that even when it is in place inside the nasogastric tube, there is still room to pass enteral nutriment through the nasogastric tube into the stomach. FIG. 1C illustrates schematically the proximal end of the apparatus. The proximal end of the flexible tube comprises a connector or junction 220 that can connect it to an external control/readout device 300 that is configured to convert the signal passed from the temperature measuring device to a temperature readout. In preferred embodiments, the control/readout device includes computing means such as a preprogrammed computer or chip that is configured to convert the temperature inside the stomach at time t after enteral nutriment is injected into the stomach.

In some embodiments of the invention, flexible tube 200 is an integral part of the feeding tube. As non-limiting examples, the flexible tube can be a lumen extending through the wall of the feeding tube, either parallel to or spiraling around the longitudinal axis of the feeding tube; or the flexible tube can be physically attached to an internal or external wall of the feeding tube. In preferred embodiments of the invention, the flexible tube and/or the temperature measuring devices are thermally insulated so that the temperature of the injected enteral nutriment does not change while it is flowing into the stomach and so that the results of the measurements and calculations are not affected by the temperature and heat of the body outside of the stomach. In some embodiments of the invention, the distal end of the flexible tube comprises a plurality of openings Non-limiting examples of such embodiments include a distal end that is in the shape of a ring with holes on the distal side, or a flat distal end with a plurality of holes in a geometry akin to that of a shower head.

In contrast to systems known in the art for determination of gastric content volume, in which the enteral nutriment is injected via the feeding tube, in the system disclosed herein, the enteral nutriment is injected via the flexible tube, which has a much smaller diameter than the feeding tube. This difference enables use of much smaller quantities of injected material at temperatures much closer to body temperature. Thus, in contrast to literature methods in which each injection typically comprises about 50 cm$^3$ at a temperature of about 1° C., in typical embodiments of the present invention, less than 20 cm$^3$ of water at a temperature of 10-25° C. (i.e. less than 30° C., and typically about 20° C., below body temperature) are injected. In preferred embodiments of the invention, the volume of water injected is 1-5 cm$^3$. The use of significantly smaller quantities of material enables the method to be performed much more frequently than in literature methods. In addition, the use of a tube of small diameter and the injection of the enteral nutriment under pressure cause the enteral nutriment to be ejected from the flexible tube at higher velocities than are typical of methods known in the art, so that the enteral nutriment injected through the flexible tube mixes rapidly with the stomach contents, typically in less than 60 s, preferably in less than 30 s.

Figure 2:
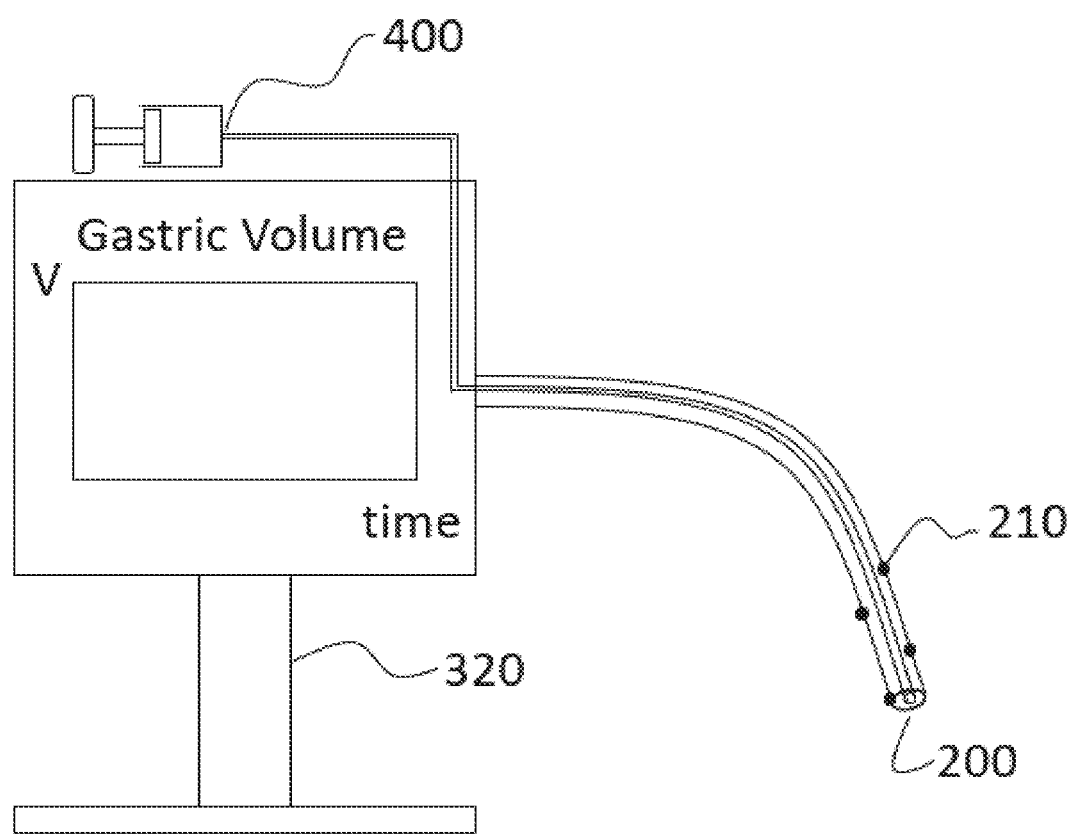
FIG. 2 presents a photograph of one embodiment of apparatus of the present invention.

Reference is now made to FIG. 2, which shows a photograph of one embodiment of the apparatus of the instant invention. Flexible tube 200 is shown inside nasogastric tube 110 and partially extending from the ends of the nasogastric tube, with thermistor 210 connected to the distal end of the flexible tube. Also shown are control/measurement electronics 320 for converting the thermistor signal to a temperature readout, connected to the proximal end of the flexible tube. As shown in the figure, the entire apparatus fits within the nasogastric tube and yet leaves sufficient room surrounding the flexible tube such that enteral nutriment can be injected (e.g. by use of syringe 400) unimpeded.

While the examples shown in FIGS. 1 and 2 are of embodiments in which the feeding tube used is a nasogastric tube, it should be emphasized that the method disclosed herein does not depend on the type of feeding tube used, and can be used with any type of feeding tube.

In some embodiments of the invention, the apparatus includes communicating means for communicating a signal proportional to the calculated gastric volume. In preferred embodiments, the communicating means comprise a connection configured to transmit a signal to a control system for automatic feeding means such as a feeding pump by which a signal proportional to the calculated gastric volume can be passed (e.g. from the control/measurement electronics 320) to the control system of the automatic feeding means. The communicating means may be of any appropriate type known in the art, e.g. a wired or wireless data connection, an electrical connection for passing a voltage or current proportional to the calculated volume of enteral nutriment, etc. In these embodiments, when the apparatus herein disclosed is connected via this connection to the control system of the feeding apparatus, the feeding apparatus can thereby be programmed to provide enteral nutriment in response to the signal received from the invention herein disclosed. As a non-limiting example, the control system of the feeding apparatus can be programmed to convert the signal received from the apparatus herein disclosed to a command signal to cause the feeding apparatus raise or lower the rate of introduction of enteral nutriment into the patient's stomach depending on the current gastric volume, e.g. to maintain the gastric volume to within predetermined bounds.

In some embodiments, the apparatus is connected to or comprises a stomach pump of any kind known in the art, and is configured to activate the stomach pump if the gastric content volume is determined to have risen at a rate above a predetermined maximum or to a volume above a predetermined maximum. As explained above, a sudden rise in gastric content volume may indicate that the patient is about to vomit. In order to prevent this even from occurring, the apparatus is configured to at least partially pump out the patient's stomach if the gastric content volume is rising too rapidly or to a value that is above a predetermined maximum.

The following examples are presented in order assist a person having ordinary skill in the art to understand how to make and use the invention herein disclosed. The examples are not intended to be limiting in any way.

Example 1

As a proof of principle of the method herein disclosed, experiments were performed in which cold water was injected into a vessel containing water held at a constant temperature.

Reference is now made to FIG. 3, which presents a graph showing the temperature of the water in the vessel as a function of time following injection of cold water, in which the apparatus herein disclosed was used to make the measurements. As can be seen, the temperature drops approximately 0.25° C. within a few seconds of the injection at time $t_0$, followed by a rise to the relatively stable pseudo-equilibrium temperature $T_f$. The temperature profile can be modeled by the mathematical relationship given in eq (1) as described above.

Example 2

A series of measurements were made in which a known volume of cold water was injected into a vessel containing water held at a constant temperature as in the previous example, and the method disclosed herein used to estimate the gastric content volume. For each injected volume, three independent estimations of the volume using the inventive were performed. The results are summarized in Table 1.

TABLE 1

| | | Actual volume (ml) | | |
|---|---|---|---|---|
| | | 250 | 500 | 750 |
| Calculated volume (ml) | 1 | 276 | 572 | 820 |
| | 2 | 242 | 595 | 554 |
| | 3 | 276 | 544 | 856 |

As can be seen from the results summarized in the table, the inventive method is quite accurate. Excluding the one obvious outlier, the average deviation of estimated volume from the true volume was 11.2% (s.d. 4.4%).

Example 3

A second series of measurements were made in which a known volume of cold water was injected into a vessel containing water in which the vessel was immersed in a constant-temperature water bath. The results of this series of measurements are summarized in Table 2.

TABLE 2

| | | Actual volume (ml) | | |
|---|---|---|---|---|
| | | 250 | 500 | 750 |
| Calculated volume (ml) | 1 | 285 | 434 | 613 |
| | 2 | 236 | 564 | 794 |
| | 3 | 188 | 589 | 691 |
| | 4 | 128 | 480 | 687 |
| | 5 | 127 | 490 | 833 |
| | 6 | 187 | 522 | 798 |

The accuracy of these measurements was also quite good; the average deviation of the estimated volume from the true volume was 15.3% (s.d. 13.7%).

Example 4

Figure 4:
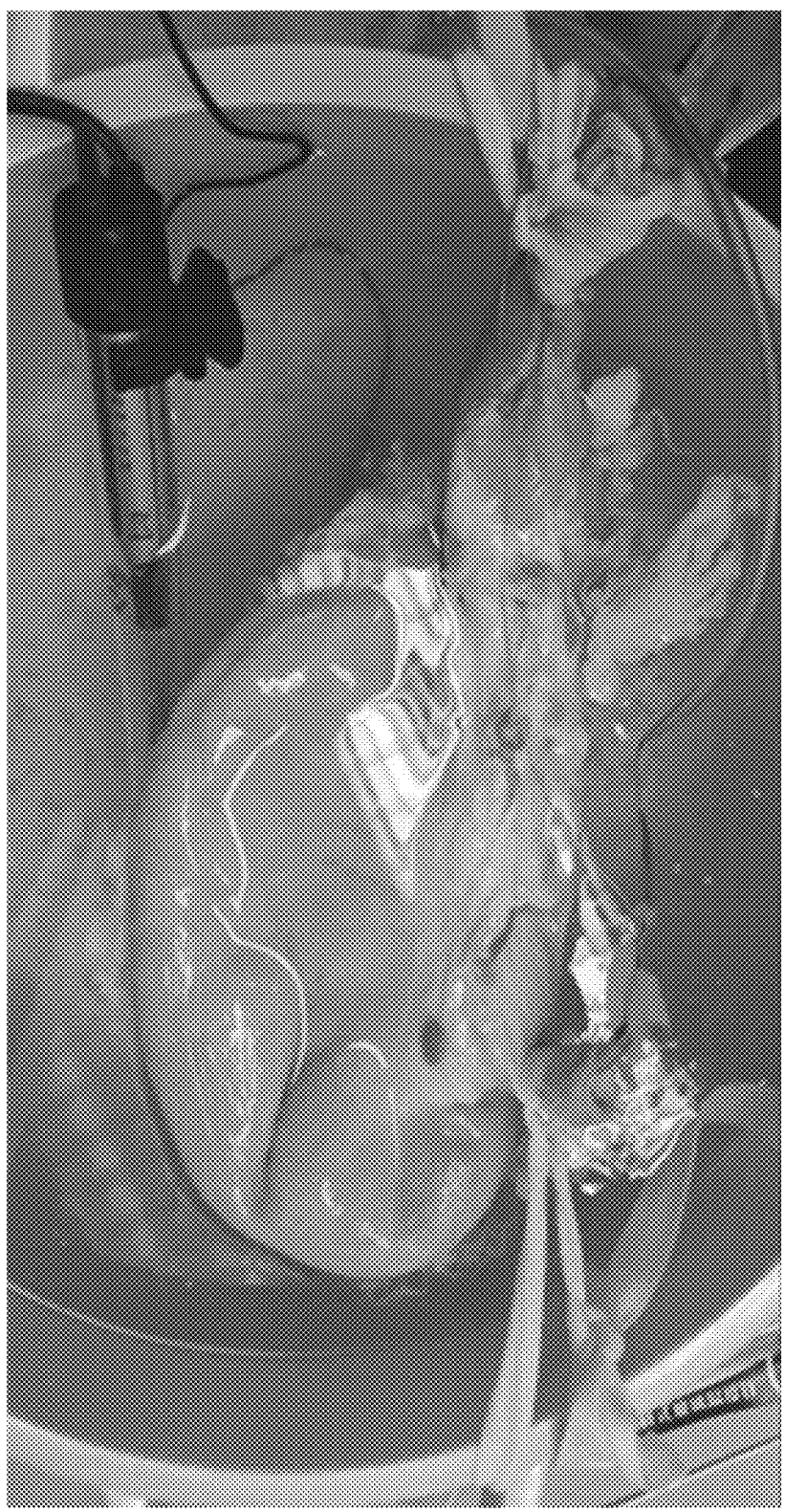
FIG. 4 presents a photograph of a system on which the inventive method was demonstrated; and, FIGS. 5A-5C present results of experiments performed using the system depicted in FIG. 4.
Figure 5A:
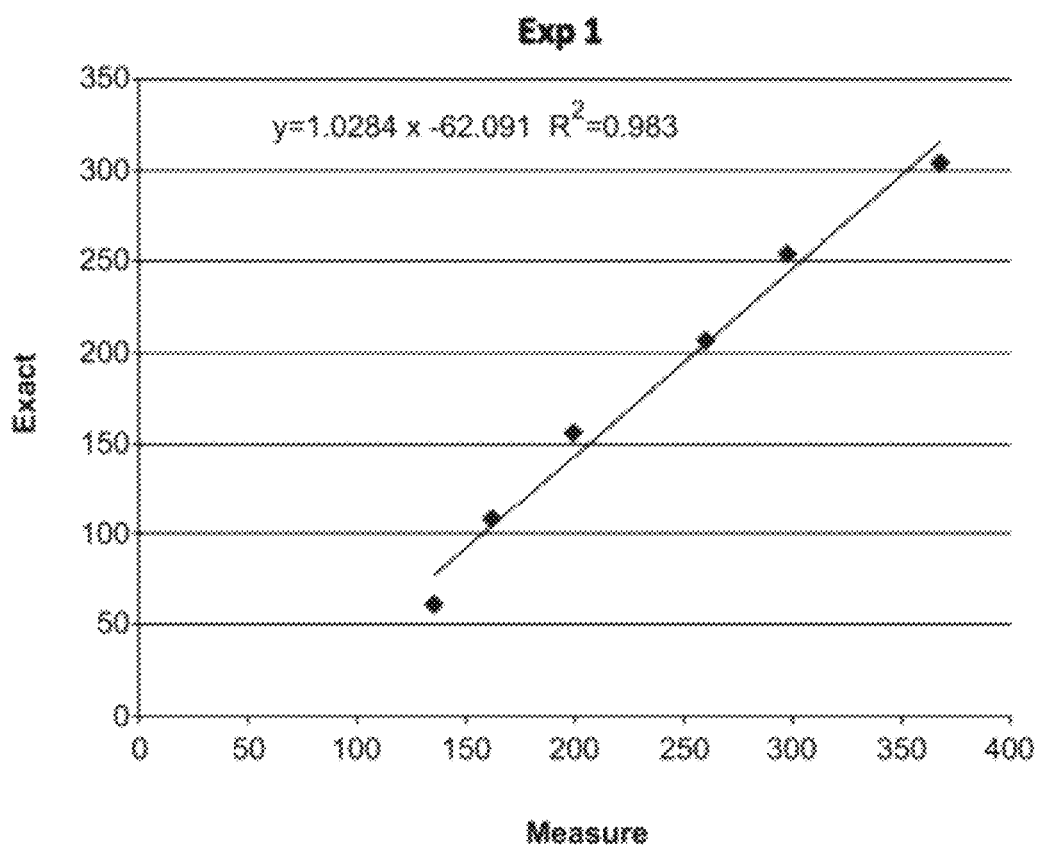
Figure 5B:
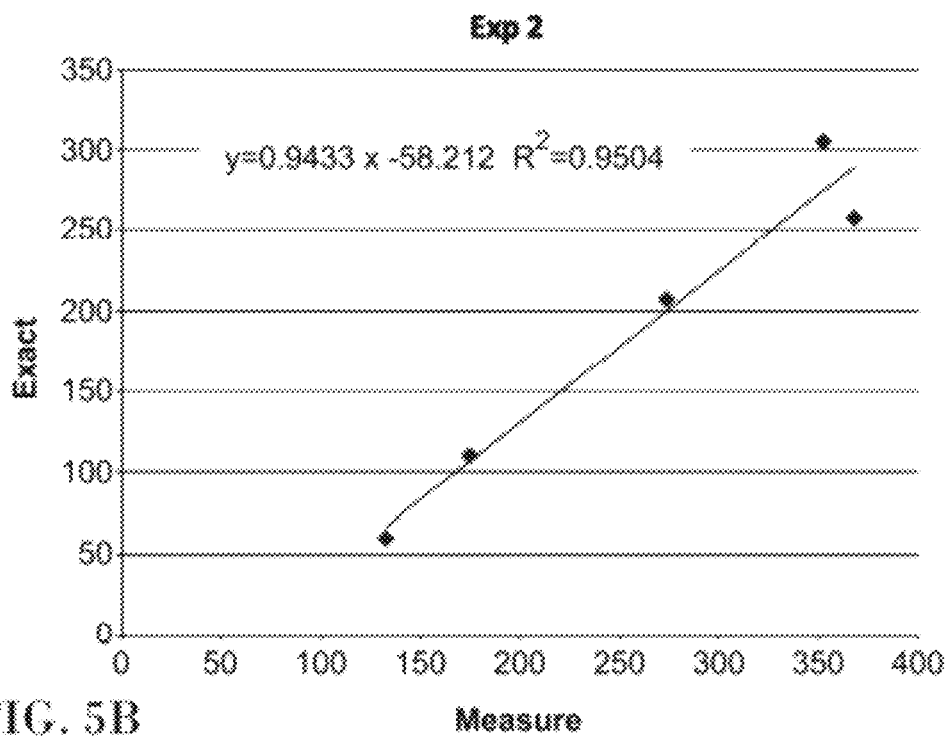
Figure 5C:
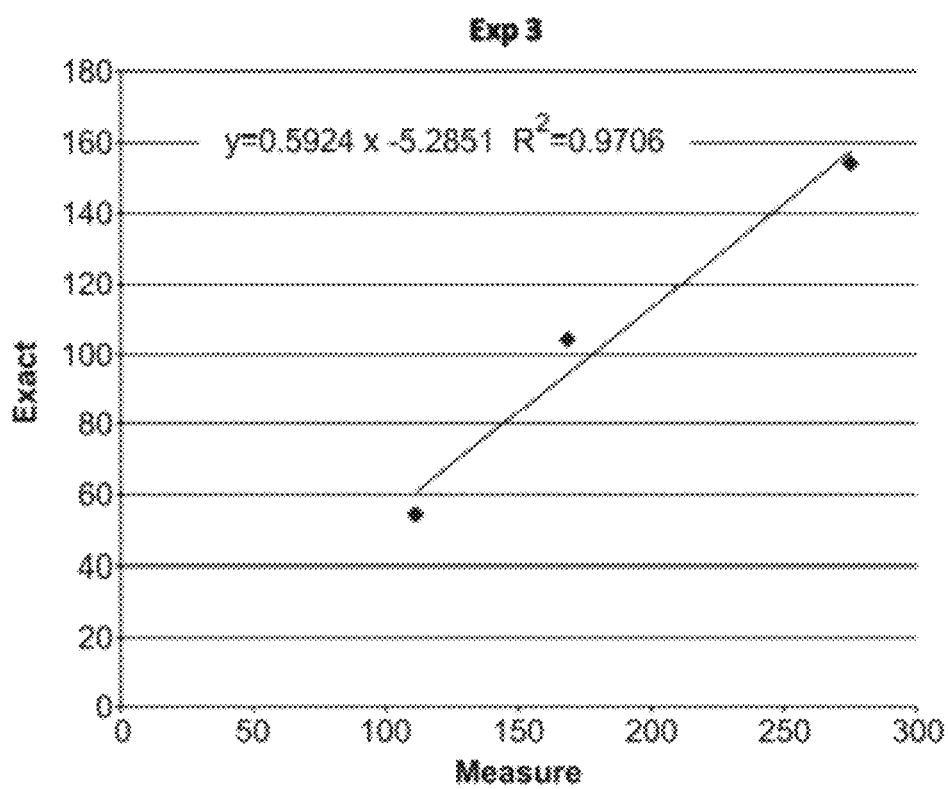

As a further demonstration of the accuracy of the inventive method, a known volume of enteric nutriment was introduced into a pig's stomach, which is similar in size and physical properties to a human stomach, held in a constant-temperature bath, and then volume then calculated by using the instant method. The experimental setup is depicted in FIG. 4. Results of three independent measurements are presented graphically in FIGS. 5A-5C. The graphs show the exact volume as a function of the volume calculated using the formula given in eq 1. As can be seen from the experimental results, there is an excellent correlation between the volume as determined by the instant method and the exact volume injected into the stomach.

We claim:

1. A method for determining gastric content volume $V_t$ in a patient, comprising:
    determining a temperature $T_0$ of said content of said patient's stomach at or prior to a predetermined time $t_0$, said content having a heat capacity $C_p^0$;
    introducing a predetermined volume $V_{in}$ of enteral nutriment at a temperature $T_{in}$, that is different than $T_0$, at or prior to said time $t_0$ and having a heat capacity $C_p^{in}$;
    measuring a temperature $T_f$ of said content of said patient's stomach at least one predetermined time t after said predetermined time $t_0$, but prior to a time at which the gastric contents return to $T_0$; and,
    calculating said gastric content volume, $V_t$, based on the equation $$V_t = \frac{C_p^{in}}{C_p^0} \cdot \frac{T_{in} - T_f}{T_f - T_0} \cdot V_{in},$$

wherein $V_{in} < 20$ cm$^3$; $|T_0 - T_{in}| \le 30°$ C.;
and, said step of introducing enteral nutriment is performed such that said enteral nutriment mixes with said content of said patient's stomach with a mixing time below a maximum time $t_{max} \le 60$ s.

2. The method according to claim 1, wherein said step of introducing enteral nutriment comprises introducing a predetermined volume of water.

3. The method according to claim 1, wherein said $V_{in}$ is between 1 and 5 cm$^3$.

4. The method according to claim 1, wherein $t_{max} \le 30$ s.

5. The method according to claim 1, wherein said enteral nutriment has a density $\rho_{in}$, and said step of determining said gastric content volume does not comprise any step selected from the group consisting of: measuring $\rho_{in}$; performing a calculation in which a value of in is explicitly included; and, performing a calculation comprising an equation in which a term explicitly depending on $\rho_{in}$ is included.

6. The method according to claim 1, wherein a relationship between said internal temperature at time t and said gastric content volume is modeled by a method selected from the group consisting of:
    using a machine learning protocol to produce a model of said relationship;
    using a machine learning protocol to refine a pre-existing model of said relationship;
    using a revaluation method to produce a model of said relationship; and,
    using a revaluation method to refine a pre-existing model of said relationship.

7. The method according to claim 1, wherein said step of measuring a temperature $T_f$ comprises independently measuring said temperature $T_f$ at a plurality of times.

8. The method according to claim 1, comprising producing at least one output signal selected from the group consisting of:
    a warning if said calculated gastric content volume is outside of predetermined limits;
    a warning if said calculated gastric content volume indicates that said patient needs to be fed;
    a warning if a time-dependent temperature profile obtained by measuring $T_f$ a plurality of times is consistent with flexible tube having been inserted into a lung of a patient;
    an output signal proportional to said calculated gastric content volume; and,
    a signal configured to direct a control system of an automatic feeding apparatus to perform an action selected from the group consisting of increasing a rate of feeding, decreasing a rate of feeding, increasing a volume of feeding, decreasing a volume of feeding, stopping feeding, and starting feeding.

9. The method according to claim 1, comprising pumping out of said stomach at least a portion of said gastric content if at least one condition exists selected from the group consisting of:

said calculated gastric content volume is observed to have increased at a rate above a predetermined maximum; and, said gastric content volume is above a predetermined maximum; is met.

10. An apparatus for determining gastric content volume, comprising:

a flexible tube comprising a proximal end and a distal end and having an outer diameter configured to fit into a nasogastric tube while leaving sufficient space for enteral nutriments to pass through and an inner diameter sufficiently so as to allow the introduction of a predetermined volume $V_{in}$ of said enteral nutriments at a temperature $T_{in}$, which is different than the temperature $T_0$ of the gastric contents at or prior to a predetermined time $t_0$, said predetermined volume $V_{in}$ of enteral nutriment having a heat capacity $C_p^{in}$ and the heat capacity of said gastric contents is $C_p^0$ prior to said introduction of a predetermined volume $V_{in}$ of said enteral nutriments;

at least one temperature measuring device attached to said flexible tube, said temperature measuring device configured to produce a temperature-dependent signal during a time period between said $t_0$ and $t_f$, where $t_f$ is at least one predetermined time t after said predetermined time $t_0$, but prior to a time at which the gastric contents return to a temperature $T_0$ being the temperature of said gastric contents at said predetermined time $t_0$;

an enteral nutriment introduction means configured to introduce a predetermined volume $V_{in}$ of enteral nutriment having a temperature $T_{in}$ into said proximal end of said flexible tube; or (ii) a control/readout means in connection with said flexible tube, said control/readout means configured to convert said temperature-dependent signal into a temperature reading; and, to determine, from a time-dependent temperature profile obtained from said temperature measuring device, whether said flexible tube has been inserted into a lung or into a stomach of a patient; or (ii) a communication means configured to communicate a signal proportional to a calculated gastric content volume to at least one external device;

wherein $V_{in}$<20 cm$^3$; |$T_0$−$T_{in}$|≤30° C., where $T_0$ is a temperature of content of said patient's stomach measured prior to introduction of said enteral nutriment; and, said enteral nutriment introduction means is configured such that said enteral nutriment can be introduced into said patient's stomach with a maximum mixing time $t_{max}$ of less than 60 s, in order to provide the temperature information in the equation $$V_t = \frac{C_p^{in}}{C_p^0} \frac{T_{in} - T_f}{T_f - T_0} \cdot V_{in},$$

11. The apparatus according to claim 10, wherein said temperature measuring device comprises at least one device selected from the group consisting of thermistors and thermocouples.

12. The apparatus according to claim 10, wherein at least one of said temperature measuring device and said flexible tube is disposable.

13. The apparatus according to claim 10, wherein said flexible tube is incorporated integrally into a nasogastric feeding tube.

14. The apparatus according to claim 10, wherein said distal end of said flexible tube comprises a plurality of openings.

15. The apparatus according to claim 10, comprising a device configured to alter a temperature of content within a stomach, said device disposed at said distal end of said flexible tube.

16. The apparatus according to claim 10, wherein said enteral nutriment introduction means are configured to introduce enteral nutriment into a stomach of a patient at a plurality of predetermined times.

17. The apparatus according to claim 10, wherein said system comprises at least one external device selected from the group consisting of:

a pump configured to pump out at least a portion of said gastric content if said temperature-dependent signal rises at a rate above a predetermined maximum; and, control means for controlling an automatic feeding apparatus.

* * * * *

UNITED STATES PATENT AND TRADEMARK OFFICE
CERTIFICATE OF CORRECTION

PATENT NO.         : 11,523,974 B2
APPLICATION NO.    : 16/461542
DATED              : December 13, 2022
INVENTOR(S)        : Samuel Shannon and Elchanan Fried It is certified that error appears in the above-identified patent and that said Letters Patent is hereby corrected as shown below:

In the Claims

Column 20, Claim 5, Line 27: after "of" please replace "in" with --$\rho_{in}$--;

Column 21, Claim 10, Line 30: please insert --(i)-- before "introduce";

Column 21, Claim 10, Line 39: Please replace "(ii)" with --(iii)--; and

Column 22, Claim 10, Line 10: please replace the equation " $V_t = \frac{C_p^{in}}{C_p^0} \frac{T_{in} - T_f}{T_f - T_0} \cdot V_{in}$ " and insert -- $V_t = \frac{C_p^{in}}{C_p^0} \cdot \frac{T_{in} - T_f}{T_f - T_0} \cdot V_{in}$ --.

Signed and Sealed this
Twenty-first Day of February, 2023

*Katherine Kelly Vidal*

Katherine Kelly Vidal
*Director of the United States Patent and Trademark Office*